(12) United States Patent
Jones et al.

(10) Patent No.: US 9,713,477 B2
(45) Date of Patent: Jul. 25, 2017

(54) DISTAL RESECTION SYSTEMS AND METHODS

(71) Applicant: Zimmer, Inc., Warsaw, IN (US)

(72) Inventors: Nolan C. Jones, Warsaw, IN (US); Jeffery A. VanDiepenbos, Syracuse, IN (US); Justin J. May, Leesburg, IN (US)

(73) Assignee: Zimmer, Inc., Warsaw, IN (US)

( * ) Notice: Subject to any disclaimer, the term of this patent is extended or adjusted under 35 U.S.C. 154(b) by 211 days.

(21) Appl. No.: 14/149,223

(22) Filed: Jan. 7, 2014

(65) Prior Publication Data

US 2014/0194883 A1 Jul. 10, 2014

Related U.S. Application Data

(60) Provisional application No. 61/749,569, filed on Jan. 7, 2013.

(51) Int. Cl.
| | | |
|---|---|---|
| A61B 17/58 | (2006.01) | |
| A61B 17/60 | (2006.01) | |
| A61F 2/00 | (2006.01) | |
| A61B 17/15 | (2006.01) | |
| A61B 17/17 | (2006.01) | |

(52) U.S. Cl.
CPC ........ *A61B 17/155* (2013.01); *A61B 17/1764* (2013.01)

(58) Field of Classification Search
CPC combination set(s) only.
See application file for complete search history.

(56) References Cited

U.S. PATENT DOCUMENTS

| | | |
|---|---|---|
| 5,486,178 A | 1/1996 | Hodge |
| 5,662,656 A | 9/1997 | White |
| 5,720,752 A | 2/1998 | Elliott et al. |
| 7,794,467 B2 | 9/2010 | McGinley et al. |
| 7,959,637 B2 | 6/2011 | Fox et al. |

(Continued)

FOREIGN PATENT DOCUMENTS

WO WO-2014107716 A1 7/2014

OTHER PUBLICATIONS

"International Application Serial No. PCT/US2014/010473, International Search Report mailed Mar. 17, 2014", 5 pgs.

(Continued)

*Primary Examiner* — Sameh Boles
(74) *Attorney, Agent, or Firm* — Schwegman Lundberg & Woessner, P.A.

(57) ABSTRACT

The present disclosure relates to systems and methods for preparing a distal end of a femur for receiving a knee prosthesis. A method can include installing a valgus guide onto an intermedullary rod, coupling a drill guide with said valgus guide, resting a boom tip of said drill guide on a high part of the femur, drilling a hole into a distal portion of a medial condyle using a first drill hole of said drill guide and drilling a hole into a distal portion of a lateral condyle using a second drill hole of said drill guide, and, subsequent to drilling the first and second drill holes, resecting the distal portion of the medial condyle of the femur and the distal portion of the lateral condyle of the femur. A system can include a valgus guide, a drill guide, and a resection tower, among other things.

27 Claims, 9 Drawing Sheets

(56) References Cited

U.S. PATENT DOCUMENTS

| | | |
|---|---|---|
| 8,277,450 B2 | 10/2012 | Dees, Jr. et al. |
| 8,333,772 B2 | 12/2012 | Fox |
| 2006/0195111 A1 | 8/2006 | Couture |
| 2006/0241634 A1* | 10/2006 | Tuttle ................ A61B 17/1675 606/86 R |
| 2007/0213738 A1 | 9/2007 | Martin et al. |
| 2010/0094301 A1 | 4/2010 | Dees et al. |
| 2010/0241126 A1 | 9/2010 | Ghijselings |
| 2011/0251618 A1 | 10/2011 | Mcallister et al. |
| 2013/0012941 A1 | 1/2013 | Dee's, Jr. et al. |

OTHER PUBLICATIONS

"International Application Serial No. PCT/US2014/010473, Written Opinion mailed Mar. 17, 2014", 7 pgs.

"International Application Serial No. PCT/US2014/010473, International Preliminary Report on Patentability mailed Jul. 16, 2015", 9 pgs.

* cited by examiner

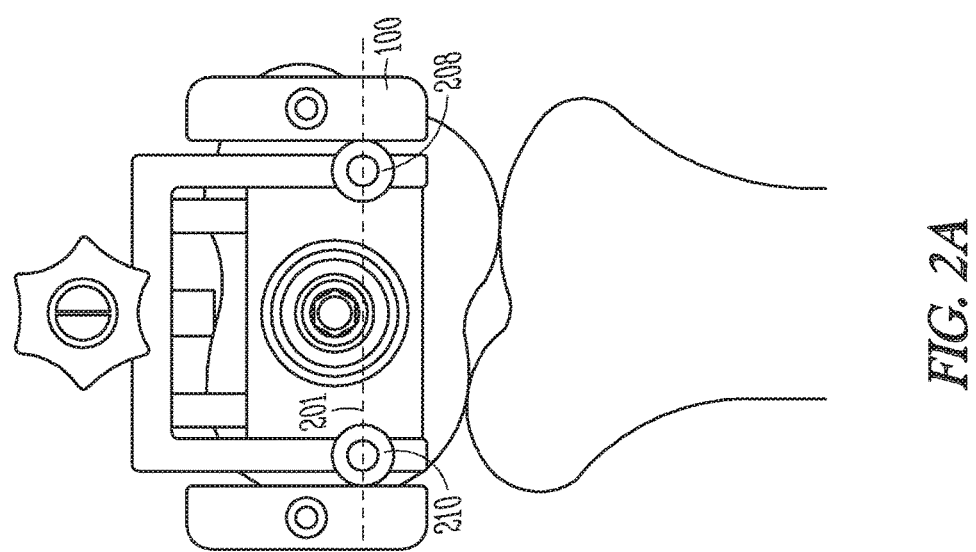

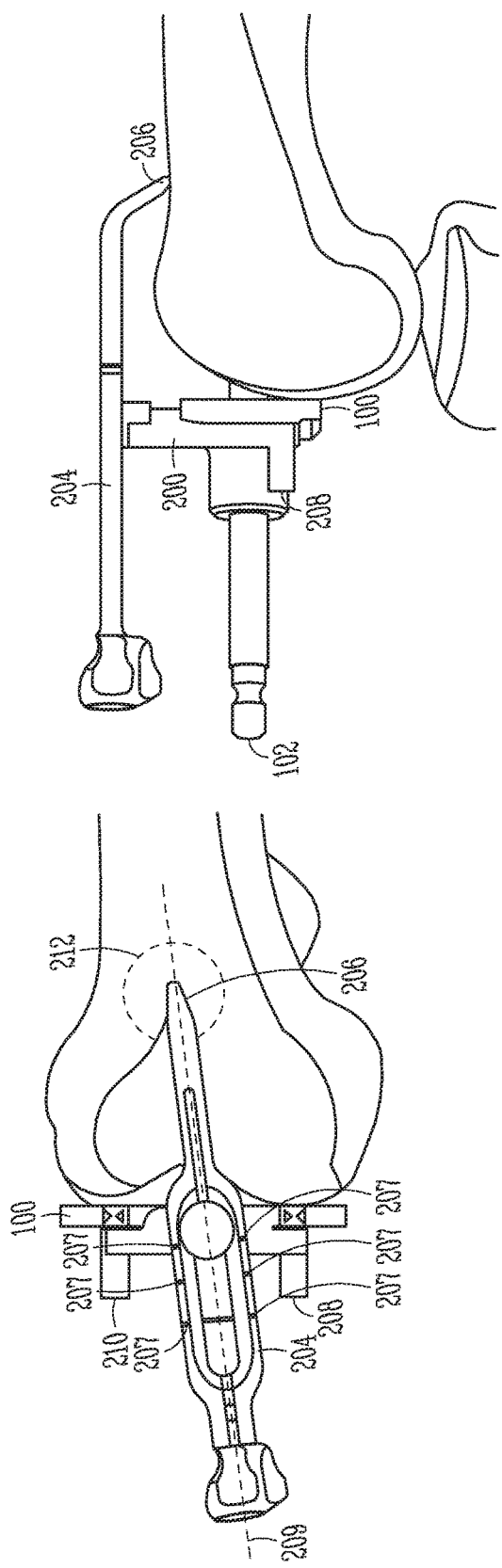

DISTAL RESECTION SYSTEMS AND METHODS

CROSS-REFERENCE TO RELATED APPLICATIONS

This application claims priority under 35 U.S.C. §119(e) from U.S. Provisional Application Ser. No. 61/749,569, filed Jan. 7, 2013, the entirety of which is incorporated by reference as if fully set forth herein.

TECHNICAL FIELD

The present disclosure relates to systems and methods for preparing a distal end of a femur for receiving a knee prosthesis.

BACKGROUND

Orthopedic prostheses are commonly utilized to repair and/or replace damaged bone and tissue in a human body. For example, a knee prosthesis can include a femoral component that is configured to replace the articular surface of one or both of the natural condyles at a distal end of a femur. Frequently, the femoral component articulates with a tibial component attached to a proximal end of a patient's tibia, so that the knee prosthesis completely replaces the articular surfaces of the natural knee femur and tibia.

The surgery that is required to install knee prostheses is invasive and typically involves the use of numerous instruments to, among other things, establish femoral alignment (e.g., using a femoral valgus alignment guide); establish external rotation (e.g., using an anterior referencing femoral sizing guide); and size the femur. The use of multiple instruments often requires the surgeon to place and remove each instrument as he or she progresses through a surgical procedure. Each time, the surgeon must establish or re-establish a correct positioning for each subsequent instrument used during the surgical procedure. Establishing or re-establishing the correct positioning for each instrument can be cumbersome and time consuming. In addition, it is possible that establishing or re-establishing the correct positioning for each instrument each time it is replaced with the subsequent instrument can lead to errors in positioning and, as a result, in the improper installation of the prosthesis.

SUMMARY

The present inventors recognize that there is a need for new systems and methods for performing the installation of knee prostheses that include fewer instruments, fewer steps, and/or less time to accomplish the installation of the prostheses. The embodiments of the present systems and methods accomplish this goal.

The present systems and methods are configured for preparing a distal end of a femur for receiving a knee prosthesis. A method can include installing a valgus guide onto an intermedullary rod, coupling a drill guide with said valgus guide, resting a boom tip of said drill guide on a high part of the femur, drilling a hole into a distal portion of a medial condyle using a first drill hole of said drill guide and drilling a hole into a distal portion of a lateral condyle using a second drill hole of said drill guide, and, subsequent to drilling the first and second drill holes, resecting the distal portion of the medial condyle of the femur and the distal portion of the lateral condyle of the femur. The method can further include decoupling said drill guide from said valgus guide and replacing said drill guide with a resection tower. A system can include a valgus guide, a drill guide, and a resection tower, among other things.

To better illustrate the systems and methods disclosed herein, a non-limiting list of embodiments is provided here:

In Embodiment 1, a method for preparing a distal end of a femur for receiving a knee prosthesis comprises installing a valgus guide, including a first aperture for slidably accepting an intramedullary rod and one or more second apertures for accepting a drill guide, onto the intramedullary rod such that it contacts at least a distal portion of a medial condyle of the femur; coupling said drill guide with said valgus guide, including sliding one or more drill guide posts into said one or more second apertures of the valgus guide and locating a first drill hole of the drill guide substantially over the distal portion of the medial condyle of the femur and a second drill hole of the drill guide substantially over the distal portion of the lateral condyle of the femur intramedullary; resting a boom tip of said drill guide on a high part of the femur to align said first drill hole and said second drill hole; drilling a hole into the distal portion of the medial condyle using said first drill hole and drilling a hole into the distal portion of the lateral condyle using said second drill hole; and resecting the distal portion of the medial condyle of the femur and the distal portion of the lateral condyle of the femur subsequent to drilling said first drill hole and said second drill hole.

In Embodiment 2, the method of Embodiment 1 is optionally configured such that locating the first and second drill holes over the distal portion of the medial and lateral condyles of the femur includes orienting the first and second drill holes along an axis substantially parallel to an axis of the intramedullary rod.

In Embodiment 3, the method of any one or any combination of Embodiments 1 and 2 optionally further comprises decoupling said drill guide from said valgus guide and replacing said drill guide with a resection tower. The resection tower includes a distal cut guide and one or more posts configured to slide into said one or more second apertures on the valgus guide.

In Embodiment 4, the method of Embodiment 3 is optionally configured such that resecting the distal portion of the medial and lateral condyles of the femur includes inserting a saw blade into the distal cut guide of the resection tower.

In Embodiment 5, the method of any one or any combination of Embodiments 1-4 optionally further comprises coupling a cut guide with the distal end of the femur, including inserting a first post of the cut guide into the hole drilled into said distal portion of the medial condyle and inserting a second post of the cut guide into the hole drilled into said distal portion of the lateral condyle.

In Embodiment 6, the method of Embodiment 5 optionally further comprises verifying a size of the femur before coupling the cut guide with the distal end of the femur.

In Embodiment 7, the method of any one or any combination of Embodiments 1-6 is optionally configured such that resting the boom tip on the high part of the femur includes establishing femoral alignment and external rotation.

In Embodiment 8, the method of any one or any combination of Embodiments 1-7 optionally further comprises coupling a knee prosthesis with the distal end of the femur.

In Embodiment 9, a system comprises a valgus guide including a first aperture for slidably accepting an intramedullary rod and one or more second apertures; a drill guide, couplable with the valgus guide, including one or more drill guide posts, the one or more drill guide posts sized and shaped to be received by the one or more second apertures of the valgus guide; and a resection tower, couplable with the valgus guide, including one or more tower posts, the one or more tower posts sized and shaped to be received by the one or more second apertures of the valgus guide.

In Embodiment 10, the system of Embodiment 9 optionally includes a boom tip.

In Embodiment 11, the system of any one or any combination of Embodiments 9 and 10 is optionally configured such that said drill guide includes a first drill hole and a second drill hole, the first and second drill holes are positioned on said drill guide to be respectively located over a distal portion of medial and lateral condyles when said drill guide is coupled with said valgus guide.

In Embodiment 12, the system of Embodiment 11 optionally further comprises one or more drill bits sized and shaped to be received by the first and second drill holes.

In Embodiment 13, the system of any one or any combination of Embodiments 9-12 is optionally configured such that an orientation of an axis of the first aperture and an orientation of an axis of each of the one or more second apertures of said valgus guide are parallel.

In Embodiment 14, the system of any one or any combination of Embodiments 9-13 is optionally configured such that said resection tower includes a distal cut guide.

In Embodiment 15, the system of Embodiment 14 optionally further comprises a saw blade sized and shaped to be received by the distal cut guide.

In Embodiment 16, system or method of any one or any combination of Embodiments 1-15 is optionally configured such that all elements or options are available to use or select from.

These and other examples and features of the present systems and methods will be set forth in part in the following Detailed Description. This Summary is intended to provide non-limiting embodiment of the present subject matter—it is not intended to provide an exclusive or exhaustive explanation. The Detailed Description below is included to provide further information about the present systems and methods.

BRIEF DESCRIPTION OF THE DRAWINGS

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present document.

FIGS. 2A-2D are diagrams of a valgus guide installed onto an intramedullary rod and a drill guide coupled with said valgus guide.

DETAILED DESCRIPTION

Figure 1:
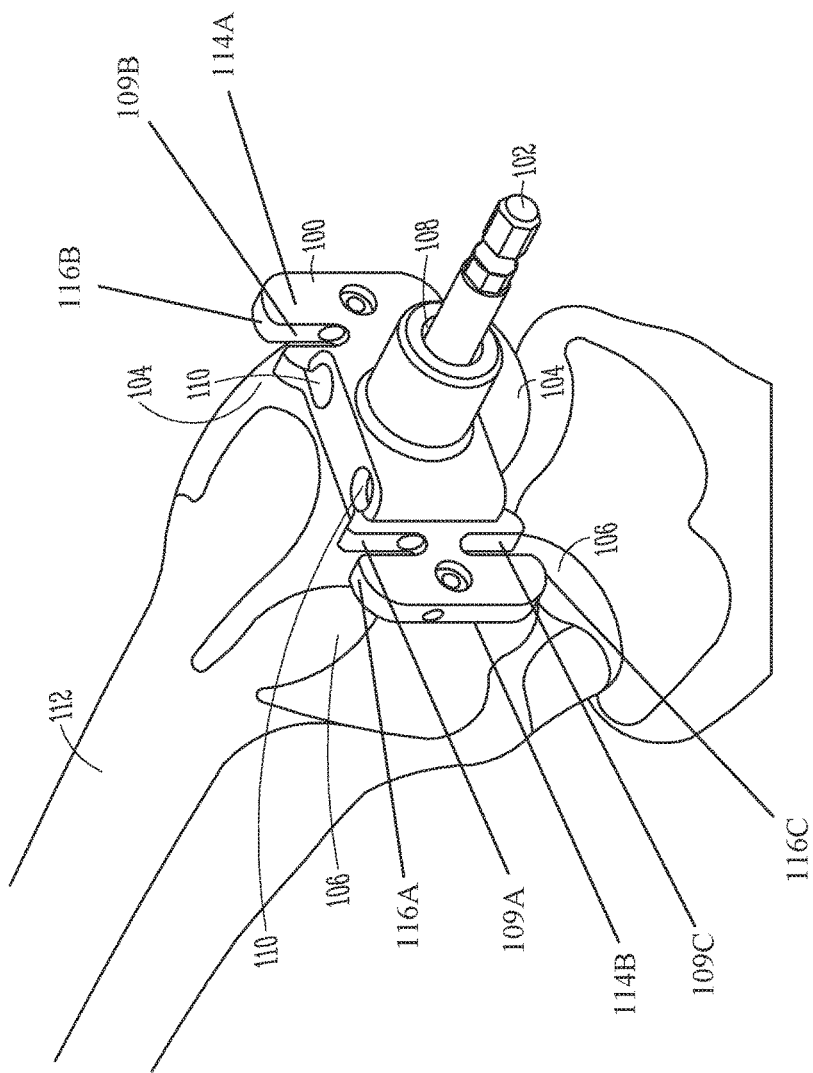
FIG. 1 is a diagram showing a valgus guide installed onto an intramedullary rod.
Figure 2:
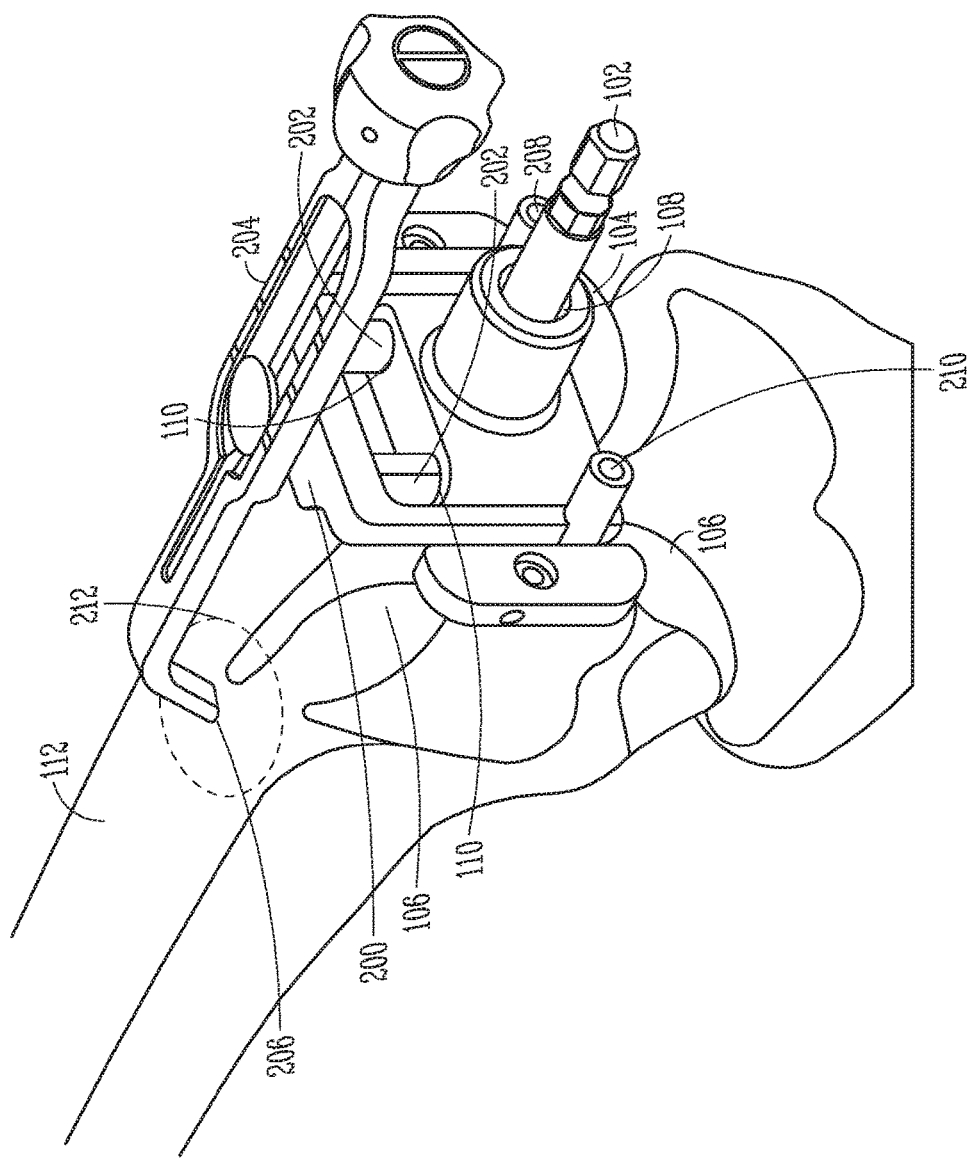
FIG. 2 is a diagram of a valgus guide installed onto an intramedullary rod and a drill guide coupled with said valgus guide.
Figure 2B:
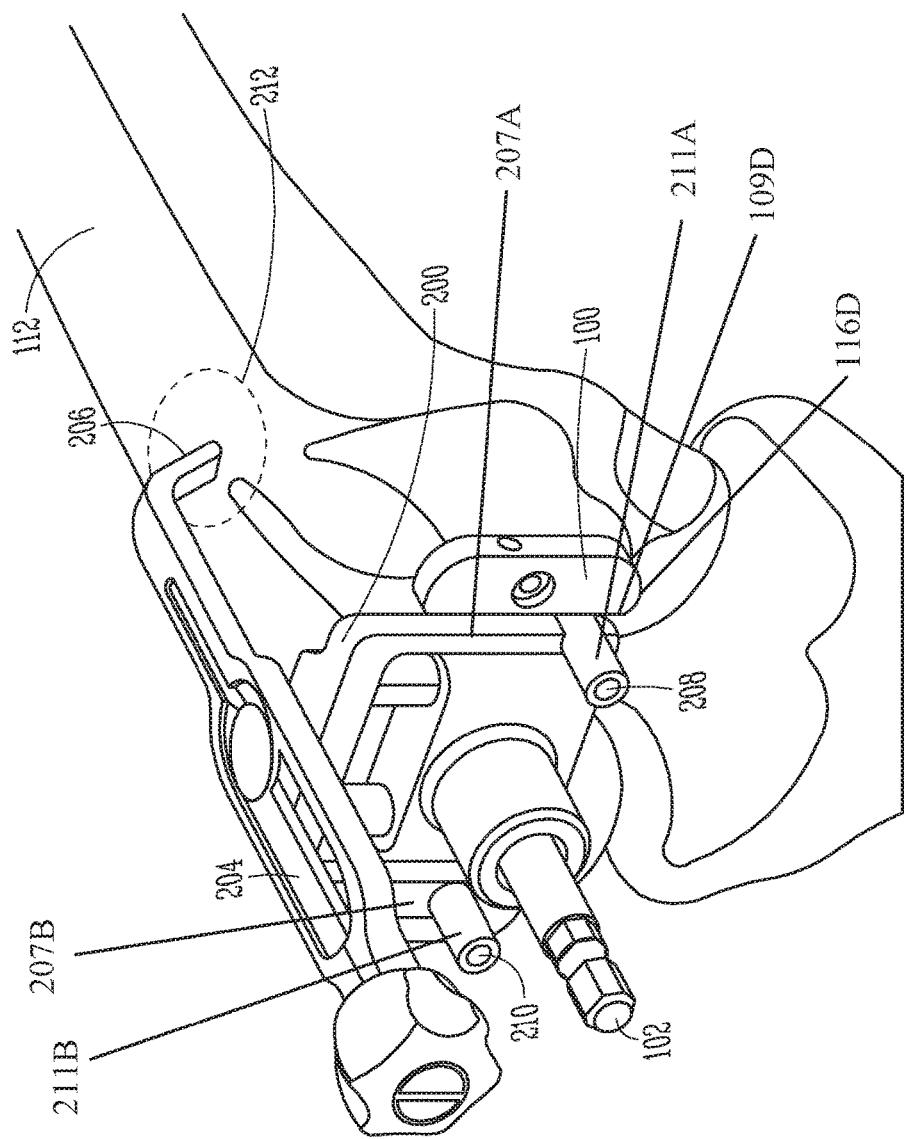

The embodiments hereinafter disclosed are not intended to be exhaustive or limit the invention to the precise forms disclosed in the following description. Rather the embodiments are chosen and described so that others skilled in the art can utilize its teachings.

This description is intended to be read in connection with the accompanying drawings, which are to be considered part of the written description of the embodiments of the present invention. The drawing figures are not necessarily to scale and certain features of the invention may be shown exaggerated in scale or in somewhat schematic form in the interest of clarity and conciseness.

Making reference to FIGS. 1, 2, and 2A-2C, embodiments of the present invention relate to systems and methods for preparing a distal end of a femur 112 for receiving a knee prosthesis. A method, including the use of system components, can comprise:

(i) installing a valgus guide 100 onto a femoral intramedullary rod 102, such that it contacts at least a distal portion of a medial condyle 104 of the femur 112, wherein said valgus guide 100 comprises a first aperture 108 for slidably accepting the intramedullary rod 102, a first set of opposing slots 109A and 109B, a second set of opposing slots 109C and 109D (see FIG. 2B), and one or more second apertures 110 for accepting a drill guide 200 (see FIG. 2), said valgus guide 100 further comprising first and second opposing major surfaces 114A and 114B, and a plurality of edge surfaces 116A, 116B, 11C and 116D;

(ii) installing said drill guide 200, wherein said drill guide comprises one or more drill guide posts 202 configured to slide into said one or more second apertures 110 of the valgus guide 100; a boom 204, having a boom tip 206; a first arm 207A and a second arm 207B, having a first drill hole 208 and a second drill hole 210, respectively, each coupled to a tube 211A and 211B, respectively, configured to accept a drill bit (not shown), said first drill hole 208 and said second drill hole 210 located at either side of the first aperture 108, each oriented along an axis parallel or substantially parallel to the intramedullary rod 102, and said first drill hole 208 located substantially over the distal portion of the medial condyle 104 of the femur 112 and said second drill hole 210 located substantially over the distal portion of the lateral condyle 106 of the femur 112;

(iii) resting the boom tip 206 approximately on a high part 212 (area demarcated by the broken circle in FIG. 2) of the distal femur 112 to align said first drill hole 208 and second drill hole 210, thereby establishing femoral alignment and external rotation;

(iv) drilling a hole into the distal portion of the medial condyle 104 using said first drill hole 208 and drilling a hole into the distal portion of the lateral condyle 106 using said second drill hole 210 (drilled holes not shown; but see FIG. 4); and (v) resecting the distal portion of the medial condyle 104 of the femur 112 and the distal portion of the lateral condyle 106 of the femur 112 subsequent to drilling said first drill hole and said second drill hole.

In some embodiments, the valgus guide 100 contacts a distal portion of a medial condyle 104 of the femur 112 and a distal portion of a lateral condyle 106 of the femur 112.

Once the valgus guide 100 is installed onto the femoral intramedullary rod 102, rotation may be established. In some embodiments, internal/external rotation may be established by using the valgus guide 100 rather than a separate guide, such as a femoral sizer. In some embodiments, internal/external rotation may be established by aligning the axis 201 (see FIG. 2A) between the first drill hole 208 and the second drill hole 210 such that the axis 201 is, for example, parallel to the epicondylar axis of the femur or perpendicular to Whiteside's line.

In some embodiments, the boom 204 is slidably and rotatably engaged, at notch 205 (see FIG. 2C), with the drill guide 200, such that the boom tip 206 may be located by moving the boom 204 (and the tip 206) backward or forward along axis 209 and rotating the boom 204 (and the tip 206) about notch 205. In some embodiments, the boom 204 is moved and rotated, as necessary, to position the boom tip 206 along a portion of the anterolateral ridge, about one-third to one-half "up" the peak, between the high and low point of the anterolateral ridge. In some embodiments, the boom comprises markings 207 corresponding to the femur size (e.g., sizes 1, 7, and 12, with other sizes that may be interpolated). The markings 207, in turn, correlate with the saw blade exit point for the indicated femur size.

In some embodiments, the valgus guide 100 comprises a fixed angle valgus guide or an adjustable angle valgus guide.

Figure 4:
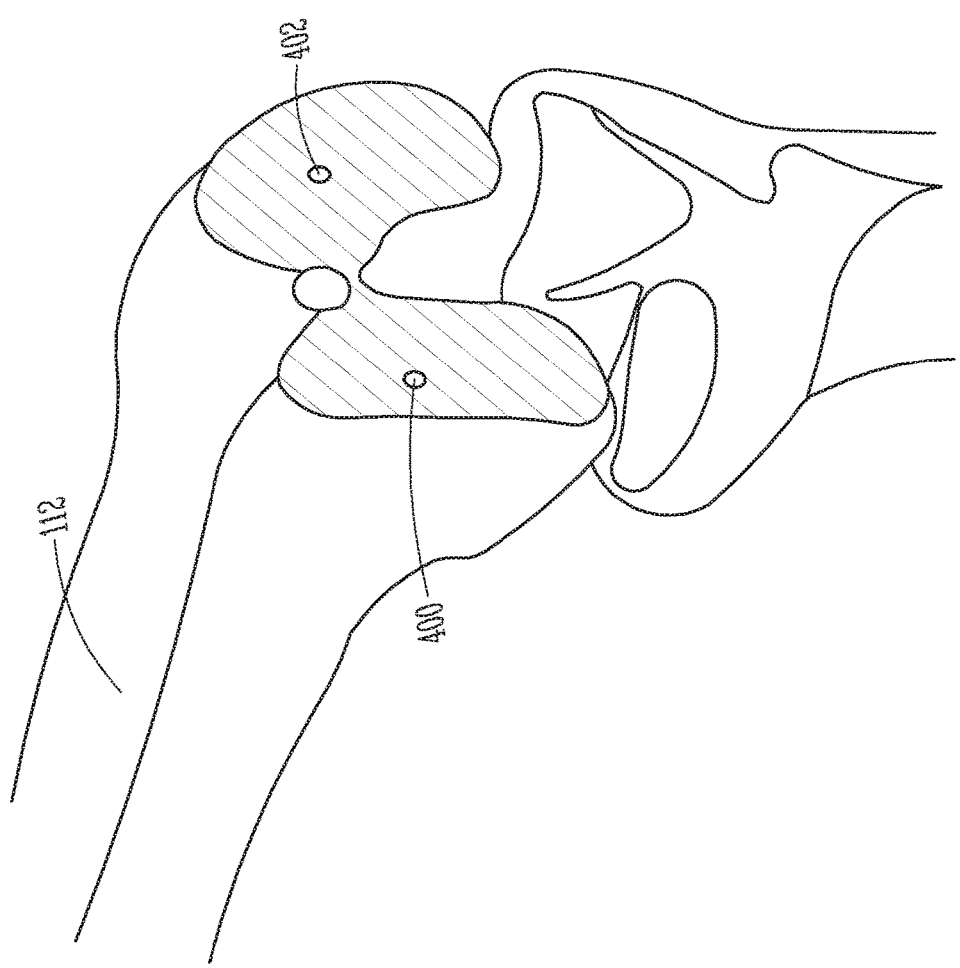
FIG. 4 is a diagram of a distal end of a femur after a portion thereof has been resected.

Making reference to FIG. 4, the resecting step recited above removes the distal portion of the medial condyle of the femur 112 and the distal portion of the lateral condyle of the femur 112. The resecting step can be performed using existing tools and methods known in the art. FIG. 4 also shows the drilled holes 400 and 402 corresponding to the holes that were drilled into the distal portions of the medial and lateral condyles using the first drill hole 208 and second drill hole 210 of the drill guide 200, respectively.

Figure 3:
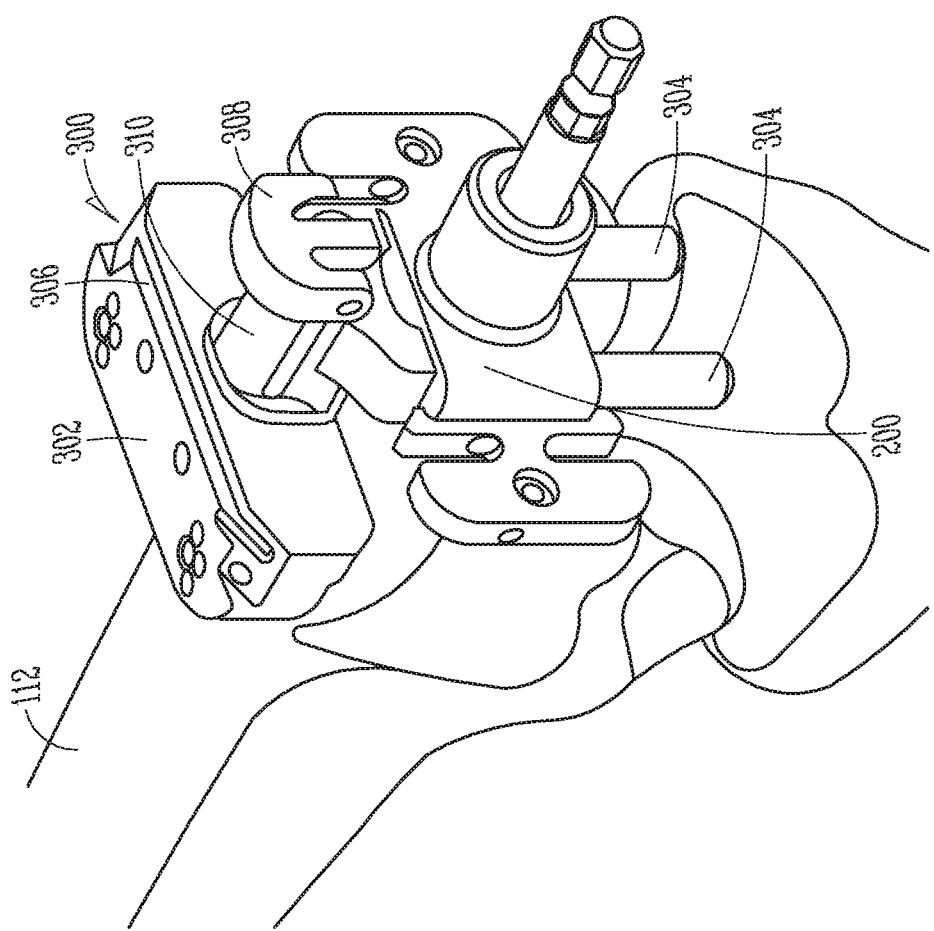
FIG. 3 is a diagram of a valgus guide installed onto an intramedullary rod and a resection tower coupled with said valgus guide.

Making reference to FIG. 3, in some embodiments, the resecting step further comprises removing said drill guide 200 and replacing said drill guide with a resection tower 300 comprising a distal cut guide 302; one or more resection tower posts 304 configured to slide into said one or more second apertures 110 on the valgus guide 200, said distal cut guide 300 comprising one or more slots 306 configured to accept a saw blade (not shown), e.g., an oscillating saw blade. In some embodiments, the distal cut guide 302 of the resection tower 300 is configured to be moveable along the same axis as the intramedullary rod 102, so as to allow for adjustment of the cutting depth; that is, how deeply one can cut into the distal portion of the femur 112. The cutting depth can be adjusted by setting the toggle 308 to an unlocked position (toggle shown in a locked position in FIG. 3). When the toggle 308 is in the unlocked position, the distal cut guide 302 can translate along shaft 310 from a minimum resection depth to a maximum resection depth. As those of skill in the art will appreciate, when the distal cut guide 302 is set to the minimum resection depth, the amount of the distal portion of the femur, which includes the distal portion of the medial condyle 104 of the femur 112 and the distal portion of the lateral condyle 106 of the femur 112, will not be as large as when the distal cut guide 302 is set to the maximum resection depth. When the distal cut guide 302 is set to the minimum resection depth, that corresponds, in some embodiments, to a 10 mm distal resection. In some embodiments, the maximum resection depth corresponds to a 14 mm distal resection.

Those of skill in the art will appreciate that the toggle 308 can be replaced by any other mechanism that allows the distal cut guide 302 to translate along shaft 310 from a minimum resection depth to a maximum (or deeper) resection depth.

Figure 5:
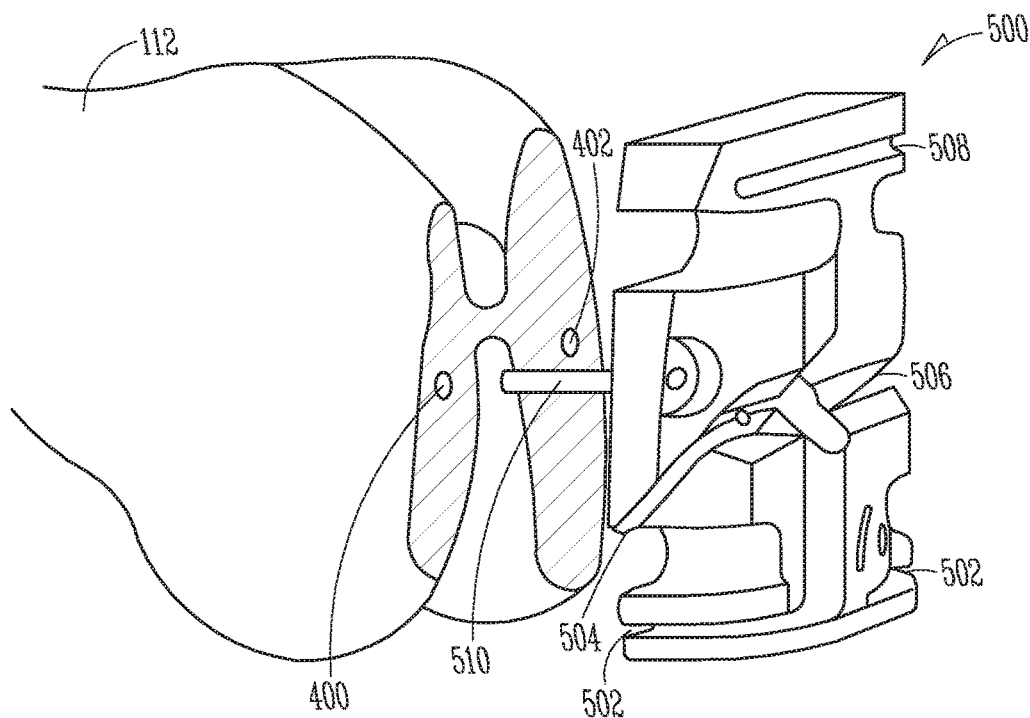
FIGS. 5-5A are diagrams of a cut guide being installed onto a distally resected femur.
Figure 5A:
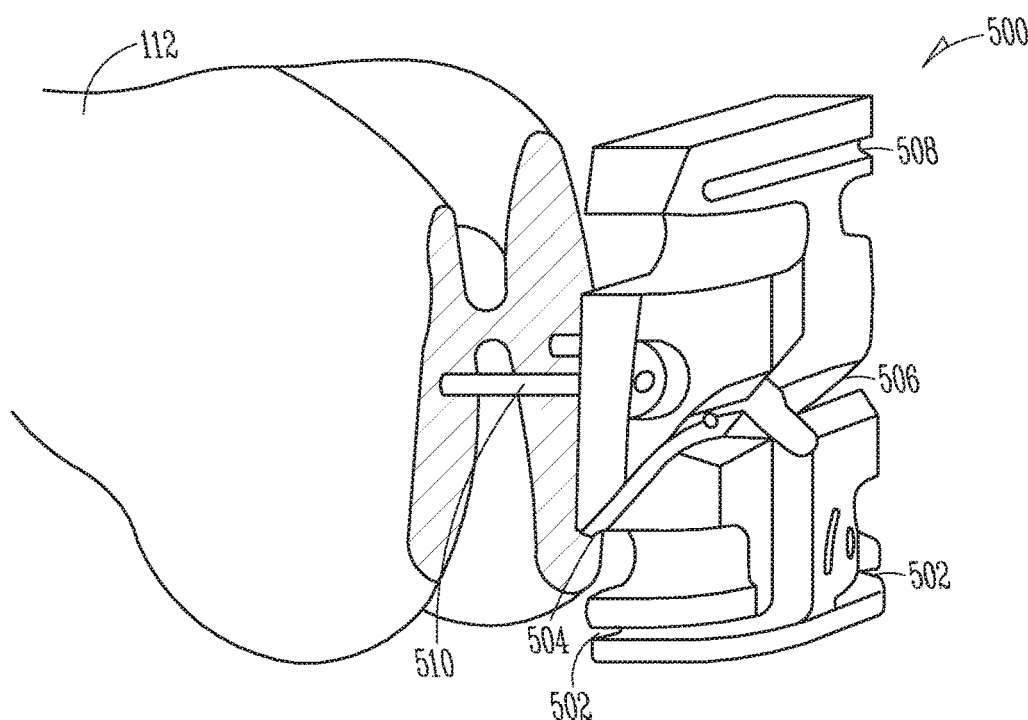
Figure 6:
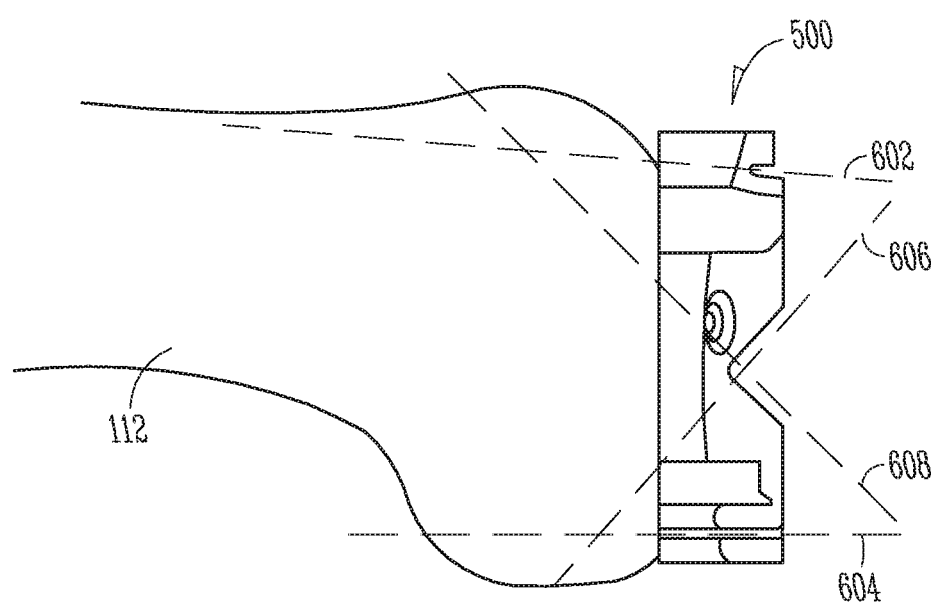
FIG. 6 is a diagram of a cut guide installed onto a distally resected femur.

Making reference to FIG. 5, in some embodiments, the method for preparing a distal end of a femur for receiving a knee prosthesis further comprises installing a cut guide 500 comprising one or more slots 502, 504, 506, and 508 configured to accept a saw blade and first and second cut guide posts 510 (only one shown in FIG. 5), said first post 510 configured to fit into the hole 400 drilled into the distal portion of the lateral condyle and said second post (not shown) configured to fit into the hole 402 drilled into said distal portion of the medial condyle. Making reference to FIG. 6, the slots 502, 504, 506, and 508 accept a saw blade and are used to perform an anterior resection 602, a posterior resection 604, a posterior chamfer resection 606, and an anterior chamfer resection 608, respectively.

In some embodiments, the size of the femur is optionally verified prior to installing the cut guide 500.

As mentioned previously, the method for preparing a distal end of a femur for receiving a knee prosthesis of the embodiments of the invention improves upon some known systems and methods for performing the installation of knee prostheses because it requires fewer instruments, fewer steps, and less time to accomplish the installation of the prostheses. For example, one known method requires sizing the distal femur (after cutting) with at least one instrument, before setting the external rotation using at least a second instrument. Another known method requires establishing femoral alignment with at least one instrument; sizing the distal femur (after cutting) with at least a second instrument; and setting the external rotation with at least a third instrument. Finally, another known method requires setting the external rotation with at least one instrument; establishing femoral alignment with at least a second instrument, and sizing the femur with at least a third instrument. In contrast, the method for preparing a distal end of a femur for receiving a knee prosthesis of the embodiments of the invention sets external rotation and femoral alignment with one instrument and effectively sizes the distal femur with the same instrument, though the sizing may be verified for good measure.

Embodiments of the invention described and claimed herein are not to be limited in scope by the specific embodiments herein disclosed, since these embodiments are intended as illustration of several aspects of the disclosure. Any equivalent embodiments are intended to be within the scope of this disclosure. Indeed, various modifications of the embodiments in addition to those shown and described herein will become apparent to those skilled in the art from the foregoing description. Such modifications are also intended to fall within the scope of the appended claims.

The Abstract is provided to allow the reader to quickly ascertain the nature of the technical disclosure. It is submitted with the understanding that it will not be used to interpret or limit the scope or meaning of the claims.

What is claimed is:
1. A system comprising:
  a valgus guide including:
    first and second opposing major surfaces configured to be disposed parallel to a resected surface of a distal femur;
    a first aperture extending between the first and second major surfaces for slidably accepting an intramedullary rod;
    first and second sets of opposing slots disposed approximately perpendicular to the first aperture,
      the first set of opposing slots configured to extend into edge surfaces of the valgus guide connecting the first and second opposing major surfaces on a first side of the first aperture; and the second set of opposing slots configured to extend into edge surfaces connecting the first and second opposing major surfaces of the valgus guide on a second side of the first aperture opposite the first side;

wherein the first set of opposing slots and the second set of opposing slots do not intersect each other; and wherein the first set of opposing slots and the second set of opposing slots extend through the first and second opposing major surfaces so that the first and second sets of opposing slots are configured to be adjacent to and open to bone of the resected surface of the distal femur; and one or more second apertures;

a drill guide, couplable with said valgus guide, including one or more drill guide posts, the one or more drill guide posts sized and shaped to be received by the one or more second apertures of said valgus guide; and a resection tower, couplable with said valgus guide, including one or more tower posts, the one or more tower posts sized and shaped to be received by the one or more second apertures of said valgus guide.

2. The system of claim 1, wherein said drill guide includes a boom and a boom tip.

3. The system of claim 2, wherein the boom tip is configured to rest on a high part of a femur to align a first drill hole and a second drill hole included on the drill guide.

4. The system of claim 3, wherein the first and second drill holes are positioned on said drill guide to be respectively located over a distal portion of medial and lateral condyles when said drill guide is coupled with said valgus guide.

5. The system of claim 2, wherein the boom and the boom tip are slidably engaged with regard to the drill guide.

6. The system of claim 5, wherein the boom and the boom tip are slidably and rotatably engaged with regard to the drill guide.

7. The system of claim 2, wherein the boom comprises markings corresponding to a femur size.

8. The system of claim 7, wherein the markings correlate with a saw blade exit point for an indicated femur size.

9. The system of claim 1, wherein said drill guide includes a first drill hole and a second drill hole, the first and second drill holes positioned on said drill guide to be respectively located over a distal portion of medial and lateral condyles and one of said first and second sets of opposing slots, respectively, when said drill guide is coupled with said valgus guide.

10. The system of claim 9, further comprising one or more drill bits sized and shaped to be received by the first and second drill holes.

11. The system of claim 1, wherein an orientation of an axis of the first aperture and an orientation of an axis of each of the one or more second apertures of said valgus guide are non-parallel.

12. The system of claim 1, wherein said resection tower includes a distal cut guide.

13. The system of claim 12, further comprising a saw blade sized and shaped to be received by the distal cut guide.

14. The system of claim 12, wherein the distal cutting guide is configured to be moveable along the same axis as the intramedullary rod.

15. The system of claim 14, wherein the distal cutting guide further comprises a toggle and a shaft, wherein the toggle has a locked and an unlocked position and the distal cutting guide can translate along the shaft when the toggle is in the unlocked position.

16. The system of claim 1, wherein the valgus guide is a fixed angle valgus guide.

17. The system of claim 1, wherein the valgus guide is an adjustable angle valgus guide.

18. The system of claim 1, wherein said first drill hole and said second drill hole are located at either side of the first aperture, each of said first and second drill holes are oriented along an axis parallel or substantially parallel to an intramedullary rod.

19. The system of claim 18, wherein the first drill hole is configured to be located substantially over a distal portion of a medial condyle of a femur and said second drill hole is configured to be located substantially over a distal portion of a lateral condyle of the femur.

20. The system of claim 1, wherein the valgus guide is configured to establish internal/external rotation.

21. The system of claim 1, wherein said drill guide includes:
a pair of arms configured to be inserted into the one or more second apertures, respectively; and
a pair of tubes, wherein each tube includes a drill hole, the pair of tubes extending from the pair of arms, respectively, to alternatively align with one of the first and second pair of opposing slots.

22. The system of claim 1, wherein said one or more second apertures extend approximately parallel to said first and second opposing major surfaces,
said first pair of opposing slots extend into a first pair of opposing edge surfaces located on an anterior side or a posterior side of the resected surface of the distal femur so as to be disposed parallel to the resected surface of the distal femur, and
said second pair of opposing slots extend into a second pair of opposing edge surfaces located on the anterior side or the posterior side of the resected surface of the distal femur opposite the first pair of opposing slots so as to be disposed parallel to the resected surface of the distal femur.

23. The system of claim 1, wherein the one or more second apertures each comprise an enclosed channel extending between a third pair of opposing edge surfaces of the valgus guide.

24. The system of claim 1, wherein the first set of opposing slots are aligned with the second set of opposing slots in an anterior-posterior direction.

25. The system of claim 24, wherein the one or more second apertures are parallel to the first and second sets of opposing slots and offset from the first and second sets of opposing slots in a proximal-distal direction.

26. A system comprising:
a valgus guide for positioning adjacent a distal end of a femur, the valgus guide including:
a first aperture for slidably accepting an intramedullary rod in a proximal-distal direction;
first and second sets of opposing slots disposed approximately perpendicular to the first aperture in an anterior-posterior direction,
the first set of opposing slots configured to extend into edge surfaces of the valgus guide on a first side of the first aperture; and
the second set of opposing slots configured to extend into edge surfaces of the valgus guide on a second side of the first aperture opposite the first side;

wherein the first set of opposing slots and the second set of opposing slots are configured to be adjacent to and open to bone of the distal end of the femur; and one or more second apertures parallel to the first and second sets of opposing slots and offset from the first and second sets of opposing slots in the proximal-distal direction.

27. The system of claim 26, wherein the first set of opposing slots do not intersect with the second set of opposing slots.

* * * * *